United States Patent [19]

Meathrel et al.

[11] Patent Number: 5,474,065
[45] Date of Patent: Dec. 12, 1995

[54] NON-INVASIVE FETAL PROBE

[75] Inventors: William G. Meathrel; Mohammad Saleem, both of Gananoque; Shirley A. Binks, Ontario, all of Canada

[73] Assignee: Graphic Controls Corporation, Buffalo, N.Y.

[21] Appl. No.: 222,729

[22] Filed: Apr. 4, 1994

[51] Int. Cl.⁶ ............................................. A61B 5/02
[52] U.S. Cl. ........................... 128/640; 128/642; 128/643
[58] Field of Search ............................. 424/78.31, 78.35, 424/78.37, 443, 447; 607/138, 149, 152, 153; 128/639, 640, 642, 643, 641, 633, 634; 252/500, 521

[56] References Cited

U.S. PATENT DOCUMENTS

| | | |
|---|---|---|
| Re. 28,990 | 10/1976 | Hon et al. . |
| 3,750,650 | 8/1973 | Ruttgers . |
| 3,827,428 | 8/1974 | Hon et al. . |
| 4,149,528 | 4/1979 | Murphy . |
| 4,180,080 | 12/1979 | Murphy . |
| 4,299,232 | 11/1981 | Zilanti . |
| 4,301,806 | 11/1981 | Helfer . |
| 4,308,873 | 1/1982 | Maynard . |
| 4,320,764 | 3/1982 | Hon . |
| 4,437,467 | 3/1984 | Helfer et al. . |
| 4,515,162 | 5/1985 | Yamamoto . |
| 4,577,635 | 3/1986 | Meredith . |
| 4,602,640 | 7/1986 | Wada et al. ............... 128/643 |
| 4,658,825 | 4/1987 | Hochberg et al. . |
| 4,706,680 | 11/1987 | Keusch et al. . |
| 4,731,078 | 3/1988 | Stoy et al. . |

(List continued on next page.)

FOREIGN PATENT DOCUMENTS

| | | |
|---|---|---|
| 1103761 | 6/1981 | Canada . |
| 0099077 | 1/1984 | European Pat. Off. . |
| 0137500 | 4/1985 | European Pat. Off. . |
| 0248627 | 12/1987 | European Pat. Off. . |
| 2569976 | 3/1986 | France ....................... 128/642 |
| 2152808 | 4/1973 | Germany ..................... 128/643 |
| 3816190 | 8/1989 | Germany ..................... 128/642 |
| 9316259 | 2/1994 | Germany . |
| 91/07910 | 6/1991 | WIPO . |
| 91/15996 | 10/1991 | WIPO . |
| 92/04864 | 4/1992 | WIPO . |

OTHER PUBLICATIONS

N. J. Randall et al., Detection of the fetal ECG during labour by an intrauterine probe, 27th Annual Meeting of Biological Eng. Society, Oxford, UK, 2–4 Sep. 1987.

Okane et al., Non-invasive continuous fetal transcutaneous $pO_2$ amd $pCO_2$ monitoring during labor. J. Perinat. Med 17 (1989) pp. 399–410.

Schmidt, Glue fixation of the $tePco_2$ for fetal monitoring, J. Perinat. Med. 15 (1987), pp. 377–382.

Hofmeyr, A nonpenetrating fetal scalp electrode, British Journal of Obstetrics and Gynaecology, vol. 100, pp. 649–652 (Jul. 1993).

*Primary Examiner*—Angela D. Sykes
*Assistant Examiner*—Eric F. Winakur
*Attorney, Agent, or Firm*—Ratner & Prestia

[57] ABSTRACT

A non-invasive fetal probe attaching to the presenting part of a fetus and sensing at least one fetal parameter during labor and delivery. The body of the probe is formed of a conductive hydrogel which is adhesive to both wet and dry surfaces. The hydrogel is either formed into a suction cup shape or is coated on the inside surface of a suction cup shell. It is the combination of both the suction cup shape, which initially holds the probe to the fetus, and the hydrogel material, which allows for increased adhesion in the wet environment of the mother's womb, which enables the probe to be securely attached to the fetus during labor and delivery. In one specific embodiment, the probe is a non-invasive fetal heart rate probe having a maternal heart rate sensor which detects the maternal heart rate to serve as a reference and a fetal heart rate sensor for monitoring the fetal heart rate. The maternal and fetal heart rate sensors are separated by an electrical insulation material which can form the suction cup.

33 Claims, 5 Drawing Sheets

U.S. PATENT DOCUMENTS

| | | |
|---|---|---|
| 4,921,904 | 5/1990 | Sparapany et al. . |
| 4,934,371 | 6/1990 | Malis et al. . |
| 4,938,218 | 7/1990 | Goodman et al. . |
| 4,989,607 | 2/1991 | Keusch . |
| 5,002,792 | 3/1991 | Vegoe . |
| 5,025,787 | 6/1991 | Sutherland . |
| 5,124,076 | 6/1992 | Smuckler . |
| 5,139,023 | 8/1992 | Stanley et al. . |
| 5,143,071 | 9/1992 | Keusch et al. . |
| 5,183,599 | 2/1993 | Smuckler . |
| 5,184,619 | 2/1993 | Austin . |
| 5,254,338 | 10/1993 | Sakai et al. ................ 424/78.37 |
| 5,345,935 | 9/1994 | Hirsch et al. . |

NON-INVASIVE FETAL PROBE

FIELD OF THE INVENTION

The present invention relates to fetal monitoring probes and more particularly, to a non-invasive fetal probe which adheres biomedical sensors to the skin of a fetus during labor and delivery.

BACKGROUND OF THE INVENTION

During labor and delivery, the well-being of the fetus must be carefully monitored. The procedure of monitoring the fetus allows the clinician to assess the health of the fetus, detect fetal stress, and provide appropriate treatment. Both internal (or direct) and external devices and methods are used to monitor and record such fetal parameters as heart rate, blood gas composition and pH levels during labor and delivery.

A. External Methods—Fetal Heart Rate

Several forms of external methods can be used for monitoring fetal heart rate. For example, one external method includes the use of ultrasound. An ultrasound transducer produces ultrasound waves which are directed at the fetus through the mother's abdomen. The ultrasound waves are reflected off moving fetal heart valves and the returning, reflected waves are received by the ultrasound transducer. Analysis of the returning waves and the duration between transmission and reception provide information concerning the fetal heart rate.

Another external method includes the use of a phonotransducer. This method involves placing a microphone, able to detect sound waves generated by the fetal heart, on the mother's abdomen. The phonotransducer then amplifies the sounds and translates them into an electric signal which can be monitored.

Abdominal wall electrocardiography is a third type of external fetal heart rate monitoring. This method detects fetal heart rate signals through ECG electrodes placed on the mother's abdomen. Electrical signals from both the fetal and maternal hearts are detected by the ECG electrodes. The maternal signal is filtered out and the remaining fetal heart rate signals trigger a monitor to count fetal heart beats. Proper placement of the abdominal electrodes is critical in this method; absent proper placement, electrical noise from electromyographic maternal abdominal wall muscle activity may prevent a clear signal.

All of the external methods of measuring fetal heart rate have an important advantage: they are noninvasive. Consequently, these methods largely avoid adverse effects on the mother or the fetus. The quality of the fetal heart rate recording using external monitoring methods is not as good, however, as that achieved by direct methods. This is a major limitation on external monitoring methods. As a general rule, it is necessary to restrict the mother's movements during external monitoring methods to reduce extraneous signals and interferences to obtain accurate tracings. Motion artifact is so common with external techniques that it is virtually impossible to obtain readable tracings unless logic data processing is used. Valuable information about fetal heart rate variability may be lost through such processing.

B. Direct Methods—Fetal Heart Rate

In direct fetal heart rate monitoring, an electrode is attached directly to the fetal presenting part. Typically, the electrode is a spiral wire or hook which penetrates (is inserted directly into) the fetal epidermis and holds the fetal probe in position. The primary advantage of a direct monitoring system of this kind is that the electrode detects the fetal cardiac electrical signal without interference which occurs when detecting the signal through another medium such as the mother's abdomen. The fetal cardiac electrical signal is a precise signal, allowing for accurate assessment of the fetal heart rate and any variations in that rate. Further, during direct fetal heart rate monitoring maternal movement is less restricted during the monitoring without compromising the tracing.

The limitation on this direct fetal heart rate monitoring method is that it is an invasive technique, exposing the mother and the fetus to the potential of injury, infection, or both. Injury may take the form of trauma (such as hemorrhage at the attachment site) to the skin, face, eyes, or other parts of the fetus. In addition, invasive attachment can threaten the life of the fetus by exposing the fetus to maternal body fluids containing infectious components. Venereal diseases and viruses such as acquired immune deficiency (AIDS) and hepatitis B can be transferred directly to the fetus. Moreover, the sharp wire or hook exposes the patient (mother) and clinician to potential injury.

C. Non-Invasive Direct Methods

Various techniques have been described attempting to obtain the benefits of direct fetal monitoring while avoiding the risks attendant invasive penetration of the fetal epidermis. Fetal blood gas analysis has been used to assess fetal health during labor. Blood gas analysis is typically done in a clinical laboratory on blood drawn from the fetus during labor (clearly an invasive technique). Alternatively, Okane et al., "Non-invasive continuous fetal transcutaneous $pO_2$ and $pCO_2$ monitoring during labor," Journal Perinatal Medicine, 17(6), 399 (1989), describe non-invasive continuous fetal transcutaneous $pO_2$ and $PCO_2$ monitoring during labor. Okane et al. used a commercially available device, the Micro Gas 7640 probe, available from Kontron Incorporated of Everett, Massachusetts. This probe is fixed to the fetal head using a suction ring connected to a vacuum pump which maintain a negative pressure of 200–300 mm Hg. The sensor is large and requires cervical dilation of 4 cm or more before insertion is possible. The large size of the sensor and the need to apply continuous suction, through an attached vacuum line, are deterrents to the use of the sensor.

Glue fixation of a transcutaneous $pCO_2$ electrode for fetal monitoring has been described by S. Schmidt, "Glue fixation of the $tcPco_2$ electrode for fetal monitoring," Journal Perinatal Medicine, 15(4), 377(1987). Glue fixation to a fetus is difficult to achieve. It requires sufficient dilation and careful preparation of the attachment site. The electrode often becomes detached during use and may need to be reapplied. In addition, trauma to the skin during removal of a sensor attached by glue is possible. Similarly, pressure-sensitive adhesives such as those used for self-adhesive bandages are hydrophobic and will not adhere to wet surfaces such as fetal skin.

Another non-invasive technique for detecting fetal ECG during labor is described by N. Randall et al., "Detection of the fetal ECG during labour by an intrauterine probe," Journal Biomedicine, (10), 159 (England 1988), and in U.S. Pat. No. 5,025,787 issued to Sutherland et al. The article and patent describe an intrauterine pressure catheter equipped with stainless steel tips which form a multi-point electrode. The intrauterine probe is inserted through the vagina into the uterine cavity. The sensor is held in contact with (but does not adhere to) the fetus by the pressure between the uterus and the fetus. The electronic signal from the sensors is processed to obtain a fetal ECG. The presence of amniotic fluid attenuates the signal from the sensors. The article points out the difficulties in obtaining accurate results due to problems with positioning the electrode tips accurately. Moreover, a degree of electrode isolation is required for optimum detection of fetal signals.

International Patent Publication Number WO 92/04864 (which claims priority of U.K. Patent Applications Number 90-20983 and Number 90-25758 by Van der Merwe) describes a fetal probe with a rigid suction cap approximately 1.5 to 2 cm in diameter. The probe incorporates a fetal heart rate sensor. A negative pressure is created in the rigid cap, by the action of a detachable piston pump, to hold the probe on the fetal skin. The pump is detached after a valve in the cap is closed. The rigid construction of the suction cap and the loss of negative pressure between the fetal skin and suction cap allow the probe to be easily detached during use.

U.S. Pat. No. 5,184,619 describes an intrauterine pressure and fetal heart rate sensor which is inserted between a fetus and the internal uterine wall following rupture of the membranes. The tubular device uses ECG electrodes as well as a pressure transducer to detect fetal heart rate and intrauterine pressure, respectively. Fetal heart rate is detected through the amniotic fluid.

To overcome the shortcomings of the external devices; the invasive, direct devices; and the non-invasive, direct devices used to measure fetal parameters during labor and delivery, a new fetal probe is provided. An object of the present invention is to attach the fetal probe securely to the fetus in a non-invasive manner. It is still another object of the present invention to assure attachment without risk of injury to the fetus, mother, or attending personnel. An additional object is to provide a probe able to transmit a clear, unattenuated signal representative of the fetal parameter being monitored.

SUMMARY OF THE INVENTION

To achieve these and other objects, and in view of its purposes, the present invention provides a non-invasive fetal probe which adheres biomedical sensors to the skin of a fetus during labor. The invention includes a conductive assembly, made from a hydrogel formulation, which is formed into a suction cup shape and then polymerized. It is the combination of both the suction cup shape, which initially holds the probe to the fetus, and the hydrogel material, which allows for increased adhesion in the wet environment of the mother's womb. This enables the non-invasive probe to be securely attached to the fetus during labor and delivery.

The use of the hydrogel material provides several advantages over the prior art. First, because hydrogels have memory retention properties, the probe can be used with a smaller diameter guide tube (the cup can be collapsed before insertion). As a result, the fetal probe can be attached to the presenting part of the fetus earlier in labor; insertion of the smaller diameter delivery tube facilitates insertion of the probe.

Another advantage of the use of a hydrogel suction cup to adhere the fetal probe is that, in addition to having good dry adhesive properties, certain hydrogel formulations impart enhanced wet adhesive properties to the fetal probe. The use of diisopropanolamine provides these unexpected and unique wet tack properties.

The adhesive properties achieved by the probe of the present invention avoid the attachment problems of the prior art. For example, the invasive technique of attaching an electrode having a sharp hook or wire directly to the fetal epidermis, with its concomitant risks of injuring the fetus and spreading diseases and viruses, is avoided. The accurate readings afforded by the present invention also improve the quality of the results obtained relative to such prior art as external monitoring techniques and other techniques which, although non-invasive, do not securely and releasably attach a probe to the fetus.

Thus, two important aspects of the present invention are the chemical formulation of the hydrogel material used and the configuration of suction cups made from the hydrogel material itself. An additional aspect is the use of the suction cup made of the hydrogel material in combination with the delivery system—which allows for earlier application of the probe during labor due to the memory retentive properties of the cup which allow it to be used with the smaller diameter delivery tube.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
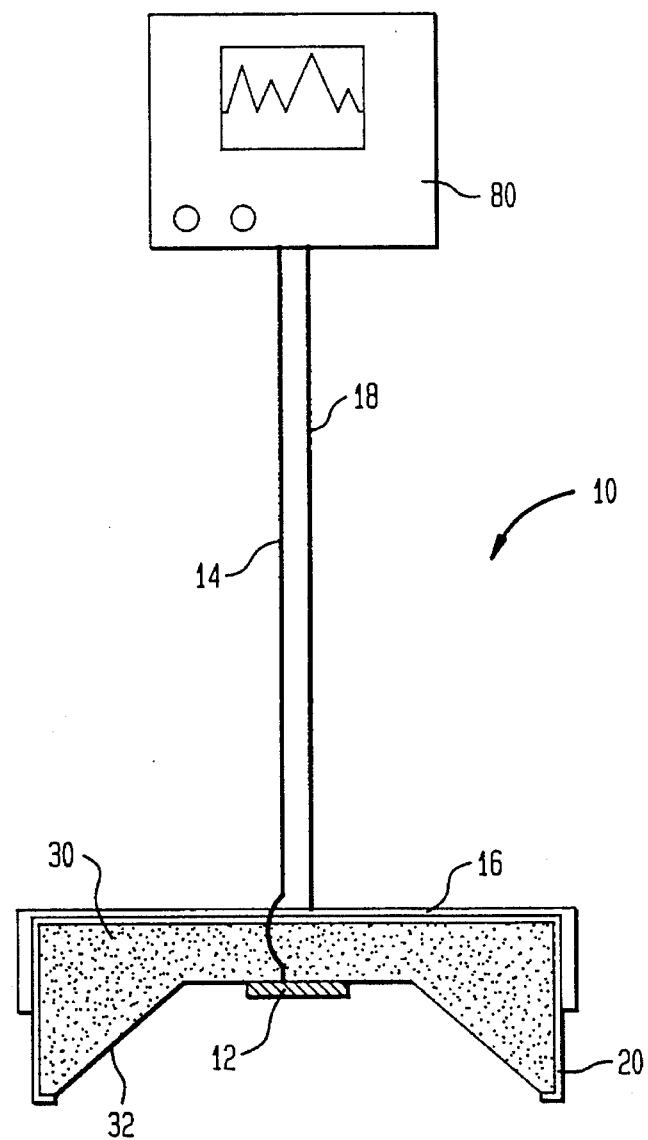
FIG. 1 is a cross section of a non-invasive fetal probe constructed in accordance with the present invention.
Figure 2:
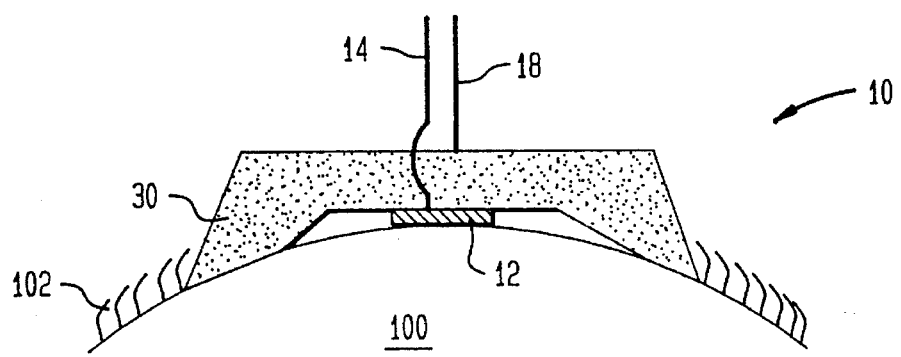
FIG. 2 is a cross section of the fetal probe shown in FIG. 1 attached to a fetus.
Figure 3:
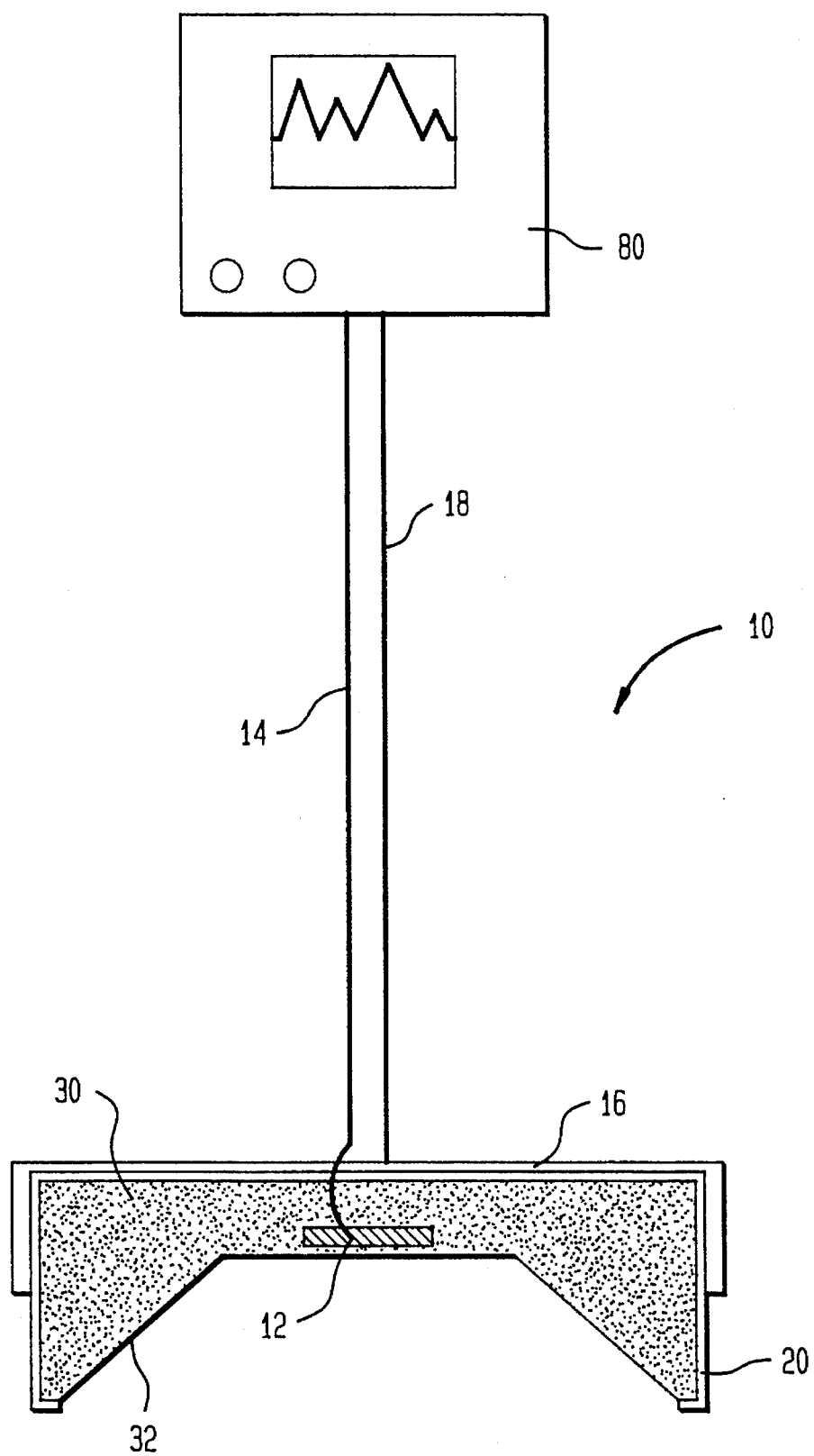
FIG. 3 is a cross section of the fetal probe of the present invention having a fetal sensor embedded in the hydrogel of the body of the fetal probe.

Referring now to the drawing, wherein like reference numerals refer to like elements throughout, FIGS. 1, 2, and 3 illustrate a non-invasive fetal probe 10 constructed in accordance with the present invention. It is emphasized that, according to common practice, the various elements of the drawing are not to scale. On the contrary, the width, length, and thickness of the various elements are arbitrarily expanded or reduced for clarity.

Fetal probe 10 is inserted through the birth canal and is attached to the presenting part (typically the head) of the fetus 100. Because it is "non-invasive," fetal probe 10 does not penetrate the fetal skin. Once attached, fetal probe 10 can continuously sense, depending upon the sensors incorporated in fetal probe 10, such fetal parameters as heart rate, blood gas composition, temperature, and pH levels during labor and delivery. Other types of sensors and test equipment or combinations of sensors and test equipment could be incorporated into fetal probe 10.

Fetal probe 10 has a fetal sensor 12 with an attached fetal sensor connector 14. A maternal sensor 16 and attached maternal sensor connector 18 may also be provided. Fetal sensor 12 and maternal sensor 16 are electrodes, and fetal connector 14 and maternal connector 18 are electric leads, when fetal probe 10 is a fetal heart rate probe. In that case, an insulating barrier 20 maintains electrical separation between fetal sensor 12 and maternal sensor 16. Maternal sensor 16 can be positioned on the top surface of probe 10 or may extend down the sides of probe 10, so long as maternal sensor 16 does not contact the fetus to which probe 10 is adhered. A body 30 provides the base to which fetal sensor 12 and maternal sensor 14 are attached and secures fetal probe 10 to fetus 100.

As shown in FIG. 1, fetal sensor 12 may be positioned on the surface of body 30. Alternatively, as shown in FIG. 3, fetal sensor 12 may be embedded in body 30. In either case, fetal sensor connector 14 and maternal sensor connector 18 connect fetal sensor 12 and maternal sensor 16, respectively, to an external monitor 80.

Suction cups are commonly used to attach items to flat surfaces. The attachment is achieved by creating a negative pressure between the flat surface and the inner, concave surface of the suction cup. The bond between the flat surface and the concave surface of the suction cup depends both upon the composition, shape, and area of the suction cup and upon the characteristics of the flat surface such as smoothness and porosity. The bond fails when the negative pressure between the two surfaces is increased to atmospheric pressure. That occurs when air leaks under the edges of the suction cup or diffuses through the suction cup into the small gap formed between the flat surface and the concave surface of the suction cup.

Strong, durable bonds between suction cups and smooth, rigid, flat surfaces such as glass can be formed by the creation of strong Van der Waals' forces due to the close proximity of the two surfaces. Moreover, suction cups adhere better to wet surfaces because the water reduces surface texture and, therefore, increases Van der Waals' interactions. On fetal skin, however, which is pliable, textured, and curved, conventional suction cups will not adhere for sufficient time to be useful for fetal monitoring applications. They fall off almost immediately when applied to fetal skin.

Fetal probe 10 of the present invention solves that problem in two ways. First, the material or composition of body 30 of fetal probe 10 is designed to provide adhesion between body 30 and fetus 100. Second, the configuration of body 30 is a suction cup designed to facilitate adhesion between suction cup 30 and fetus 100. The initial attachment of fetal probe 10 to the wet surface of fetus 100 uses the vacuum created by the suction cup configuration of body 30. Thereafter, the material used to form body 30 absorbs the moisture of the wet environment, creating strong surface adhesive properties between body 30 and the skin of fetus 100.

A. Composition of Body

Polymeric hydrogels can be soft and flexible materials. Hydrogels exhibit shape memory and will return to their original shape even after deformation. Hydrogels also have the important characteristics of biocompatibility, hydrophilicity (the ability to absorb water), and may have adhesive properties, and electrical conductivity —they mimic characteristics of living tissue.

Various compositions can be used to make a hydrogel suitable for body 30. Example compositions (by percentage) are listed in Table 1. Example 3 shows a preferred embodiment for substantially hairless fetal skin. Example 5 is a preferred embodiment for fetal skin with a significant amount of hair. Example 1, which does not contain diisopropanolamine, would not be satisfactory for an in-vivo fetus.

TABLE 1

| Component | Ex. 1 | Ex. 2 | Ex. 3 | Ex. 4 | Ex. 5 |
| --- | --- | --- | --- | --- | --- |
| Water | 15.16 | 24.82 | 38.96 | 10.7 | 37.56 |
| Acrylic Acid | 25.84 | 19.13 | 28.97 | 21.7 | 15.97 |
| Darocur 1173 | 0.47 | 0.35 | 0.35 | 0.33 | 0.35 |
| Polyethylene Glycol (400) Diacrylate | 0.13 | 0.10 | 0.10 | 0.17 | 0.15 |
| Glycerine | 53.04 | 46.80 | — | 27.8 | — |
| Colloid 121 | — | — | — | 14.9 | — |
| Diisopropanolamine | — | 7.80 | 28.12 | 13.8 | 28.12 |
| Sodium Chloride | — | 1.00 | — | — | — |
| Potassium Chloride | 5.40 | — | 3.50 | 1.0 | 3.50 |
| 27% Aqueous Sodium Hydroxide | — | — | — | 9.6 | — |
| Vinyl Pyrrolidone | — | — | — | — | 13.00 |

Each of the polymers formed in the hydrogel compositions in Table 1 can be a homopolymer of acrylic acid, copolymer of acrylic acid and acrylic acid salts, copolymers of acrylic acid and esters derived from alcoholamines, copolymers of acrylic acid and vinyl pyrrolidone, copolymers of acrylic acid and acrylates, and polymers obtained from any of the above monomer combinations. In the case of a fetus with significant amounts of hair, a formulation made with 13 percent of vinyl pyrrolidone is the preferred embodiment (Example 5). Darocur 1173 (2-hydroxy-2-methyl-1-phenyl-propane-1-one) is a photoinitiator available from Ciba Geigy. Polyethylene glycol (400) diacrylate is a crosslinking agent available under the trade name Sartomer® 344, available from the Sartomer Company of West Chester, Pa. Glycerine is a humectant and plasticizer which provides flexibility and dry tack properties. Colloid 121 a polyacrylic acid solution available from Rhone-Poulenc in Marietta, Ga. enhances wet tack, viscosity, and formability properties. Diisopropanolamine, a humectant and plasticizer, helps to neutralize the acid and gives the hydrogel good wet adhesive properties. Sodium hydroxide is added to control pH. Sodium chloride and potassium chloride are electrolytes which increase conductivity.

The preferred hydrogel composition contains an alcoholamine such as diisopropanolamine. Hydrogel compositions have been prepared, however, including other secondary and tertiary alcoholamines such as triethanolamine and diethanolamine. These compositions also have good wet adhesive properties.

U.S. Pat. No. 4,921,904 (Sparapany et al.) describes super-absorbant hydrogels which include a polyamine. Diisopropylamine is mentioned. Diisopropylamine is not the same chemical, however, as diisopropanolamine. Polyamines have a single functional atom, the nitrogen atom, whereas alcoholamines have at least two functional sites—a nitrogen atom and a hydroxyl group.

U.S. Pat. Nos. 5,124,076 and 5,183,599 issued to Smuckler teach a hydrogel adhesive composition for medical electrodes which polymerizes rapidly, preferably in less than ten seconds. Specifically, the hydrogel composition contains a mixture of an N-vinyl lactam and an acrylate monomer. The hydrogel compositions of the present invention use a single monomer, acrylic acid, or a copolymer of acrylic acid and vinyl pyrrolidone, and the polymerization time (although rapid) is of little importance.

During labor, the intrapartum fetus is exposed to amniotic fluid, vaginal fluids, and, in some cases, fetal excretions. In this wet environment, an adhesive with good wet tack properties is required. (The tack is the characteristic of the adhesive to stick to a surface.) The hydrogels produced by curing the compositions listed as Examples 2–5 in Table 1 exhibit the unique property of having both a dry and a wet tack. The alcoholamine (and, specifically, diisopropanolamine) used in the compositions provides this property.

Many adhesives, for example pressure sensitive adhesives which are used with adhesive tapes, exhibit good adhesive properties to dry surfaces. These adhesive tapes, however, typically do not adhere well to wet surfaces. U.S. Pat. No. 5,139,023 issued to Stanley et al. describes a blood glucose sensor which uses a hydrogel (hydroxypropyl cellulose, gelatin, and carbopol) to adhere the device to mucosal membranes. Such materials are unlikely to have sufficient adhesive properties to hold a device such as fetal probe 10 to a wet surface such as fetus 100.

The hydrogel compositions of the present invention also have shape memory. The shape memory characteristic enables body 30 to return to the desired concave suction-cup shape after deformation. The great flexibility of the hydrogel also allows body 30 to form a strong suction when pressed against the epidermis of fetus 100.

The attachment force which holds fetal probe 10 in place on fetus 100 must be sufficient to hold fetal probe 10 in place during labor. An attachment time of ten hours or more may be required. Further, fetal probe 10 must adhere even if fetus 100 has hair 102.

Figure 4:
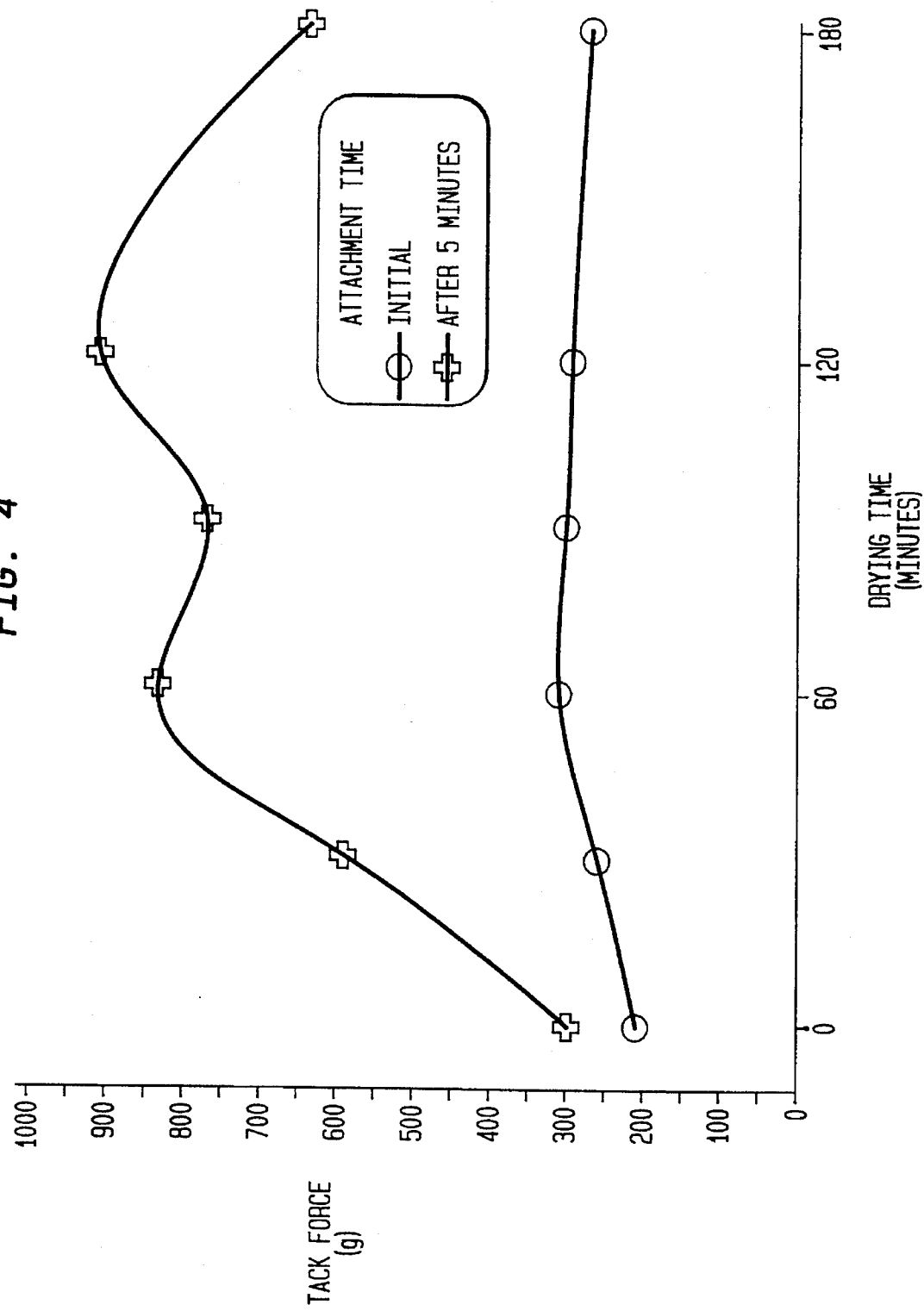
FIG. 4 is a graph of tack force (g) versus drying time (minutes) illustrating the effect of drying the hydrogel composition of Example 3, Table 1, on adhesion.

It has been found that drying the hydrogel, Example 3, Table 1 to remove some of the water from the polymer matrix can increase the tack of the hydrogel on hairy skin. FIG. 4 shows the effect of drying time on adhesion. Moreover, hydrogels prepared using vinyl pyrrolidone provide added adhesion to hairy tissue. Increased adhesion to hairy tissue has been found by replacing approximately half of the acrylic acid monomer with vinyl pyrrolidone (see Example 5 of Table 1).

Because body 30 may be used as a conductive pathway of electrical signals between fetus 100 and fetal sensor 12, body 30 must be electrically conductive as well as adhesive. The hydrogel compositions used to form body 30 meet that requirement. The hydrogel compositions of Table 1 have a 10 Hz impedance less than or equal to 2000 ohms to an impressed current of 100 microamperes. Thus, the physical and electrical properties of the hydrogel compositions can be controlled to provide a flexible, conductive, adhesive interface between fetus 100 and fetal sensor 12.

Each of the compositions listed in Table 1 may be polymerized by various means, such as ultraviolet light, heat, electron beam, redox reagents, and the like. Exposure to ultraviolet radiation is the preferred way to initiate polymerization. The hydrogel composition may be used "as is," in its form following polymerization, or the composition may be cast as a coating and then dried to provide a flexible, non-tacky, thermoplastic film.

Alternatively, the composition may be polymerized directly into a non-tacky, flexible sheet. This dry coating, flexible sheet can then be formed into the desired shape (such as a suction cup). The dry coating can be "wetted" to regain its dry and wet adhesive properties. Using the polymer as a non-tacky, dry coating on fetal probe 10 can allow for easy insertion of fetal probe 10 through the birth canal. Once in place, fluids around the fetus will reactivate the adhesive properties of the hydrogel and hold fetal probe 10 in place.

The applications for a hydrogel having good wet and dry adhesive properties are broader than a noninvasive fetal probe 10. Applications such as wound dressings and closures, transdermal drug delivery systems, ostomy adhesives, medical tapes, various medical electrodes, and the like could benefit from a hydrogel adhesive with wet and dry adhesive properties.

B. Configuration of Body

The hydrogel compositions of the present invention can be molded or formed to provide almost any desired size and shape. Body 30 can be formed by dispensing the hydrogel composition into a mold of the desired shape then polymerizing the monomers in the mold. Alternatively, suction cup-shaped probes can be prepared by spin casting, similar to the procedure used to prepare soft contact lenses.

The size and shape of body 30 formed by the hydrogel composition of the present invention affects the adhesion between body 30 and fetus 100. A suction cup shape for body 30 having a concave surface 32 contacting fetus 100 is preferred to enhance adhesion. Table 2 compares various shapes and diameters possible for body 30 and provides the 90-degree peel (the force required to peel body 30 from a flat, stainless steel plate) for each particular shape and diameter. A Shimpo Digital Force Gauge Model DF-5.0R (supplied by Shimpo America corporation of Lincolnwood, Ill. 60659) was used to make the measurements contained in Table 2.

TABLE 2

| Shape | Diameter (mm) | 90° Peel Force (g) |
| --- | --- | --- |
| Concave U | 15 | 400 |
| Concave V | 15 | 450 |
| Concave V | 20 | 710 |
| Concave V | 50 | >1075 |
| Flat | 20 | 360 |
| Convex | 30 | 720 |

Table 2 indicates that a shallow, V-shaped cup is more difficult to remove than a deeper, U-shaped cup. This additional adhesive power is beneficial toward maintaining contact during labor. Larger surfaces also have higher 90-degree peel strengths. Finally, cups with a concave shape require more force to remove them than flat and convex-shaped cups of similar size.

It is desirable for a fetal probe 10 to have a small enough diameter for ease of application early in labor. For example, a V-shaped, concave cup with a diameter of 15 to 20 mm, or which can be collapsed into a dispenser or guide tube of this diameter or less, is preferred. Such a size permits application of fetal probe 10 when cervical dilation is 1 cm or less. Fetal probe 10 need not be collapsed for insertion, as it can be placed inside a delivery tube or applied with other delivery means in an uncollapsed state.

Figure 5:
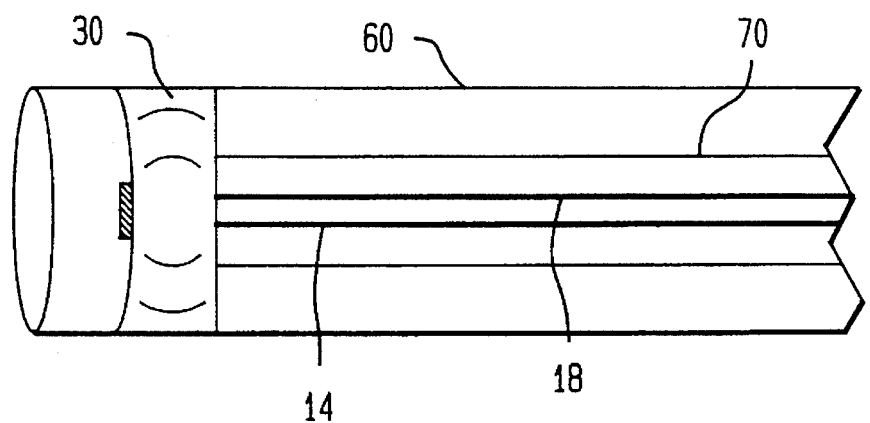
FIG. 5 is a cross section of the non-invasive fetal probe of FIGS. 1 or 3 disposed inside a guide tube in a collapsed state.

To assure both applicability of fetal probe 10 early in labor and maximum adhesive strength (larger surfaces provide more strength), the shape-retention property of hydrogel proves useful. FIG. 5 shows an exemplary embodiment of fetal probe 10 disposed inside a guide tube 60. Guide tube 60 may have a diameter of 20 mm while body 30 of fetal probe 10 has a diameter of 40 mm. Accordingly, fetal probe 10 is collapsed within guide tube 60. It will be understood that the sizes for both fetal probe 10 and guide tube 60 (or other delivery means) can be made smaller or larger, depending upon the application as will be understood by those skilled in the art.

Figure 6:
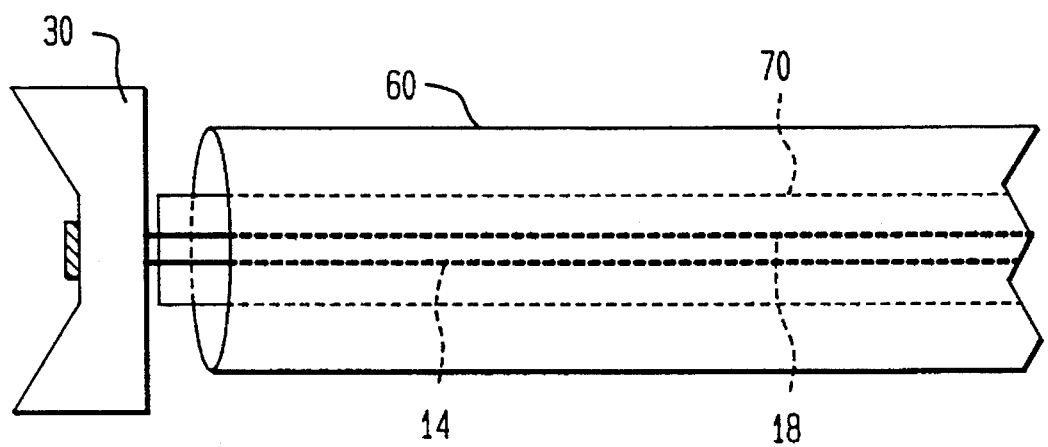
FIG. 6 is a cross section of the non-invasive fetal probe of FIGS. 1 or 3 in its normal expanded state outside of the guide tube and following expulsion from the guide tube.

Drive tube 70, which has a smaller diameter than guide tube 60, may be used to push fetal probe 10 out of guide tube 60. Once removed from guide tube 60, body 30 of fetal probe 10 regains—through the shape retention properties of the hydrogel used to form body 30—its initial, uncollapsed shape. FIG. 6 shows fetal probe 10 following ejection from guide tube 60.

In FIG. 6, it can be seen that fetal probe 10 has regained its desired, initial shape and is ready for attachment to the fetal skin. Thus, the deformation of fetal probe 10 while disposed inside guide tube 60 does not affect the shape at the time of attachment to fetus 100. Other methods of placing fetal probe 10 into contact with fetus 100 will be understood by those skilled in the art.

Body 30 may be formed entirely of hydrogel. Alternatively, body 30 may be formed of another material and only concave surface 32 of body 30 coated with a hydrogel composition of the present invention. Fetal probe 10 having body 30 so constructed shows satisfactory adhesive properties to fetus 100.

Figure 7:
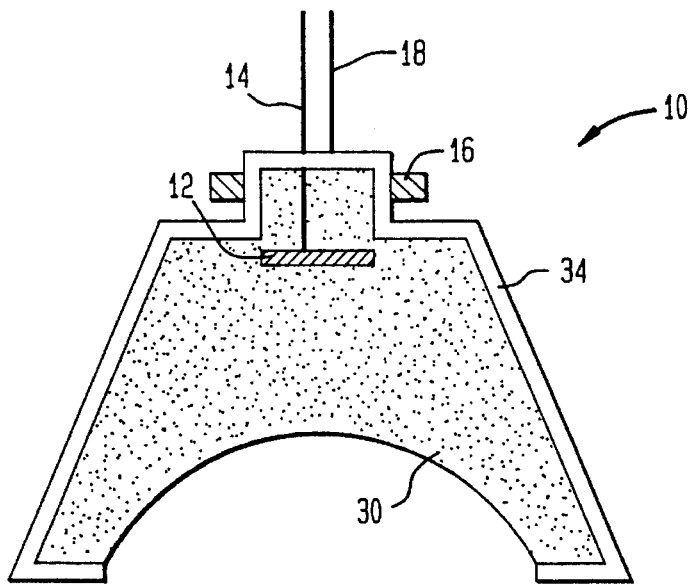
FIG. 7 is a cross section of an additional embodiment of a non-invasive fetal probe having a shell coated with hydrogel.

FIG. 7 depicts a thermoplastic shell 34 coated with hydrogel to form body 30. Shell 34 can be formed by a number of processes understood by those skilled in the art, including molding. Suitable dimensions for shell 34 are a total height of about 6.2 mm and a diameter of about 15 mm.

Various thermoplastic resins are suitable for forming shell 34. Example materials include Pellethane™ (a polytetramethylene glycol ether resin available from Dow Chemical Company, such as Pellethane 2363), Pebax™ (a polyether block amide resin available from Atochem, Inc., such as Pebax 2533) PVCs, polyurethanes and polyethylenes. Each of these materials offer different combinations of characteristics important to the manufacture and operation of fetal probe 10. Some of these characteristics are ease of molding, strength, adhesion to hydrogel, hardness water absorption, biocompatibility, price, and signal isolation.

Figure 8A:
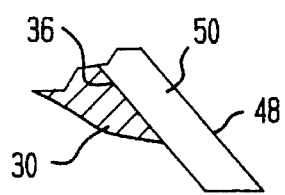
FIG. 8A is a cross section of the wall of the shell shown in FIG. 7, illustrating a straight inner wall surface.
Figure 8B:
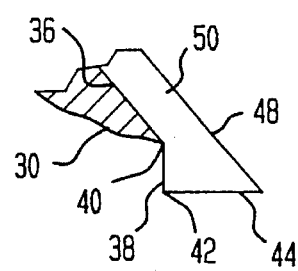
FIG. 8B is a cross section of the wall of the shell shown in FIG. 7, illustrating a ridge.
Figure 8C:
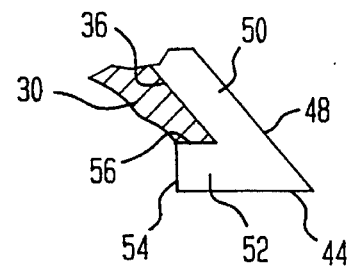
FIG. 8C is a cross section of the wall of the shell shown in FIG. 7, illustrating a ledge.

By using shell 34, the hydrogel of body 30 may be isolated from external fluids. FIGS. 8A, 8B, and 8C show three variations in the configuration of wall 50 of shell 34. FIG. 8A shows a "straight" inner surface 36, without deviations or additions, entirely parallel to the outer surface 48 of wall 50 of shell 34. FIG. 8B shows a ridge 38, which is a straight, vertical segment near the perimeter of wall 50 of shell 34. Ridge 38 has a top edge 40 and a lower edge 42. Top edge 40 is defined by ridge 38 meeting inner wall 36. Lower edge 42 is defined by bottom, horizontal surface 44 of wall 50 meeting ridge 38.

FIG. 8C shows a ledge 52, which is an extension of the wall 50 in a plane which is approximately at a 30-degree angle to outer wall 48 of shell 34. The angle of ledge 52 could be adjusted (at, for example, angles between 15 and 60 degrees) to achieve a desired holding strength. Ledge 52 has a side surface 54 and a top surface 56.

Ridge 38 of FIG. 8B and ledge 52 of FIG. 8C help to isolate the hydrogel of body 30 from external fluids by forming a seal between the hydrogel and external fluids. A fetal probe 10 constructed with ridge 38 remained attached to a simulated test "baby" for more than 32 hours while immersed in an isotonic saline solution. Ledge 52 is advantageous because it allows the hydrogel to be extended closer to the edge of shell 34.

Initial attachment of fetal probe 10 to fetus 100 uses both the vacuum effect (negative pressure) created by the suction cup shape of body 30 of fetal probe 10 and the adhesive properties of the hydrogel adhering to the wet surface of fetus 100 in the uterus. Because hydrogels have shape-retention properties, body 30 retains its suction-cup shape. As the hydrogel absorbs fluid, strong surface adhesive properties are created between the hydrogel and the fetal skin. Air will not seep under the edges of body 30, which would reduce the negative pressure under body 30, because the hydrogel adheres to fetus 100. Thus, suction cup body 30 made of the hydrogel of the present invention exhibits strong adhesive force throughout the duration of labor.

Body 30 of fetal probe 10 has a combined adhesive force generated by the adhesive properties of the hydrogel interface and the concave, suction-cup shape of the interface. Individually the adhesive force generated by the hydrogel and that generated by the geometry of the interface may be insufficient to secure attachment throughout labor. Although the combined attachment force is sufficient to hold fetal probe 10 in place during labor, it also allows detachment without injury to sensitive fetal tissue. The detachment force of fetal probe 10 from fetal tissue is in the range of 200 g to 2000 g and preferably in the range of 300 g to 1000 g.

C. Fetal Heart Rate Probe

One specific application of fetal probe 10 will be described to better illustrate the advantages of fetal probe 10. Fetal probe 10 may be used to monitor fetal heart rate without penetration of the fetal epidermis. At least four criteria affect the quality of the fetal heart rate signal monitored: (1) symmetry between the fetal and maternal (reference) electrodes, (2) maximum separation between the fetal and reference sensors, (3) maximum surface contact area to minimize impedance, and (4) stabilized connections. Application of fetal probe 10 to monitor fetal heart rate meets these criteria well.

In this application, fetal sensor 12 detects the electrical fetal heart rate signal transcutaneously. To do so, fetal sensor 12 must maintain contact with fetus 100, either directly (FIG. 1) or through the conductive hydrogel of body 30 (FIG. 3). When in direct contact with fetus 100, fetal sensor 12 may be covered with a conductive medium, such as a conductive gel, to lower impedance at the skin-sensor interface. Fetal sensor 12 must provide a sufficiently large surface area and be electrically conductive to sense the electrical fetal heart rate signal. In addition, fetal sensor 12 must be inert to chemical reaction with hydrogel and biological fluids and tissues.

A suitable material for construction of fetal sensor 12 in this application is the silver-silver chloride sensors commonly used in ECG monitoring electrodes. Fetal sensor 12 could also be formed from multi-strand stainless steel wire, such as a Teflon® coated steel wire sold by Cooner Wire in Chatsworth Calif. In one embodiment, six individual strands of 40-gauge wire were spread over concave surface 32 of body 30 to form fetal sensor 12. Such wire is very fine and light weight; therefore, it adds little mass to fetal probe 10. Alternative insulating jacket materials for the wire, other than Teflon®, could also be used.

Multi-strand carbon fiber wire is a suitable replacement for stainless steel in forming fetal sensor 2. Carbon wires are light weight and flexible. Moreover, they provide good electrical signals and do not react with hydrogel components or saline solutions. Suitable carbon wire can be obtained from Minne. Wire and Cable Company in St. Paul Minn.

In this application, fetal connector 14 is a lead wire suitable for conducting the electrical signals from fetal sensor 12 to a monitoring-signal processing unit. Fetal connector 14 passes through body 30 and maternal sensor 16 and is ultimately connected (perhaps through other wires and electrical connections) to a fetal heart rate monitor (monitor 80 shown in FIGS. 1 and 3). The environment in which fetal probe 10 is used, namely inside the uterus, requires insulation of the lead wire. The connection between fetal connector 14 and fetal sensor 12 is embedded in the conductive, adhesive hydrogel of body 30.

In this application, maternal sensor 16 must provide a sufficiently large surface area and be electrically conductive to sense the electrical maternal heart rate signal and other muscular or electrical activity. In addition, maternal sensor 16 must be inert to chemical reaction with biological fluids and tissues. Multi-strand stainless steel or carbon fiber wires, described above for use as fetal sensor 12, can also be used for maternal sensor 16. Alternatively, maternal sensor 16 may be an electrically conducting material such as a metal foil (e.g., silver, aluminum, or stainless steel) or metallized film (e.g., aluminum metallized polyester) which covers the upper surface of insulating barrier 20. Other electrically conductive, non-metallic films and coatings such as conductive carbon and conductive graphite may also be used.

Figure 9:
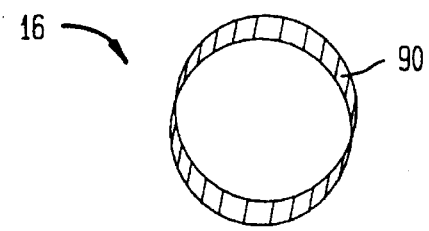
FIG. 9 shows an exemplary embodiment of the maternal sensor incorporated into the fetal probe of FIGS. 1, 3, or 7.

Maternal sensor 16 may be a band, washer, wire loop, or plate which fits on top of body 30 over insulating barrier 20. In an exemplary embodiment, as shown in FIG. 9, stainless steel band 90 can be approximately 3.5 to 4.0 mm wide (preferably 3.7 mm) and 5.0 to 5.5 mm in diameter (preferably 5.4 mm). Maternal connector 18 is a lead wire connected to maternal sensor 16 for communicating received electrical signals.

The maternal heart rate detected by maternal sensor 16 is used as a reference signal so that any maternal heart rate and other muscular or electrical signals which pass through the fetus and are detected by fetal sensor 12 can be subtracted out to provide an accurate fetal heart rate measurement. Generally, the reference component of the signal detected by fetal heart rate sensor 12 is a minor component when compared to the fetal heart rate signal. The fetal heart rate can then be isolated from the combined fetal and reference signals detected by fetal sensor 12. This is accomplished by isolating the fetal R-waves from the other signals.

Non-invasive fetal probe 10 has two leads 14, 18—similar to conventional fetal scalp electrodes—for fetal sensor 12 and maternal reference sensor 16. Both the fetal and maternal leads 14 and 18 could be replaced by a non-wired connecting system, such as a radio transmission system, to communicate information from fetal sensor 12 and maternal sensor 16 to monitoring equipment 80. A radio system would require supporting hardware as is understood by those skilled in the art.

Referring back to FIGS. 1 and 2, insulating barrier 20 serves to maintain electrical insulation between fetal sensor 12 and maternal sensor 16. Pebax a polyether block amide, is one type of insulating barrier which can serve this purpose. Other similar materials having sufficiently high dielectric properties also would suffice. Insulating barrier 20 should be flexible so as not to impede the flexibility of body 30. Ridge 38 or ledge 52 provided on wall 50 of shell 34 increases the separation of the fetal and maternal signals, which allows monitor 80 to more easily isolate the fetal heart rate signal, and helps to assure electrical isolation between fetal sensor 12 and the external fluid.

When fetal probe 10 is initially applied to fetus 100, the hydrogel of body 30 absorbs moisture and increases in tackiness. Moreover, the hydrogel swells and forces ridge 38 or ledge 52 against fetus 100—enhancing the adhesive seal between fetal probe 10 and fetus 100. Should the hydrogel absorb too much moisture and swell to the extent that it extends under shell 34, however, the seal between fetal probe 10 and fetus 100 may be adversely affected. In addition, the electric isolation between fetal sensor 12 and the external fluid would be jeopardized. Ridge 38 or ledge 52 helps to isolate the hydrogel from external fluids, thereby preventing the hydrogel from absorbing too much moisture and risking such adverse consequences.

FIGS. 1 and 3 illustrate fetal probe 10 connected to a signal processing and display unit 80. Signal processing and display unit 80 is used, in this application, to monitor the fetal heart rate detected by fetal probe 10. Signal processing display unit 80 contains the digital signal processing equipment and control instructions necessary to discriminate the fetal heart rate signal from the other extraneous signals. Signal processing display unit 80 may also carry out, in other applications for fetal probe 10, blood gas analysis, oximetry measurements, and other functions.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, although the fetal probe 10 of the present invention has been described in detail for attachment of non-invasive fetal heart rate sensors, fetal probe 10 could also be used for other sensors such as blood gas analyzers and oximetry sensors. If so, fetal connector 14 and maternal connector 18 may constitute fiber optics rather than lead wires.

What is claimed:

1. A non-invasive fetal probe adapted for attachment to the presenting part of a fetus and monitoring at least one fetal parameter during labor and delivery, said probe comprising:

a body having a concave surface forming a suction cup adapted for securing the probe to the fetus to be monitored, and being comprised of a conductive hydrogel which is prepared from a precursor composition comprising acrylic acid and an alcoholamine and is adhesive under both wet and dry conditions;

a sensor carried by said body and detecting at least one fetal parameter; and means for communicating the fetal parameter detected by said sensor from said sensor to a monitor.

2. A non-invasive fetal probe as recited in claim 1 wherein said alcoholamine of said hydrogel of said body is diisopropanolamine.

3. A non-invasive fetal probe as recited in claim 2 wherein said hydrogel of said body is prepared from water, acrylic acid, a photoinitiator, a crosslinking agent, diisopropanolamine, and an electrolyte.

4. A non-invasive fetal probe as recited in claim 3 wherein said hydrogel of said body is prepared from about 35–40% water, 15–30% acrylic acid, 0.3–0.4% photoinitiator, 0.05–0.20% crosslinking agent and 25–30% diisopropanolamine.

5. A non-invasive fetal probe as recited in claim 4 wherein said hydrogel of said body is prepared from about 39% water, 29% acrylic acid, 0.35% 2-hydroxy-2-methyl-1-phenyl-propane-1-one, 0.10% polyethylene glycol (400) diacrylate and 28% diisopropanolamine.

6. A non-invasive fetal probe as recited in claim 3 wherein said hydrogel of said body is prepared from about 38% water, 16% acrylic acid, 0.35% 2-hydroxy-2-methyl-1-phenyl-propane-1-one, 0.15% polyethylene glycol (400) diacrylate and 28% diisopropanolamine and 13% vinyl pyrrolidone.

7. A non-invasive fetal probe as recited in claim 1 wherein said body is "V"-shaped.

8. A non-invasive fetal probe as recited in claim 1 wherein said body has a diameter of 10–20 mm.

9. A non-invasive fetal probe as recited in claim 1 wherein said body further comprises a shell, said conductive hydrogel coated on said shell and forming said concave surface of said body facing the fetus.

10. A non-invasive fetal probe as recited in claim 9 wherein said shell is polymeric.

11. A non-invasive fetal probe as recited in claim 9 wherein said shell has an outer perimeter forming a member which is one of a ledge and a ridge isolating said conductive hydrogel from fluids in the environment surrounding the probe.

12. A non-invasive fetal probe as recited in claim 11 wherein said member formed by said outer perimeter of said shell is a ridge having a top edge and a lower edge and wherein said conductive hydrogel extends to said top edge of said ridge.

13. A non-invasive fetal probe as recited in claim 11 wherein said member formed by said outer perimeter of said shell is a ledge having a side surface, a top surface, and a bottom surface and wherein said conductive hydrogel is disposed on said top surface.

14. A non-invasive fetal probe adapted for attachment to the presenting part of a fetus and monitoring at least one fetal parameter during labor and delivery, said probe comprising:
- a body having a concave surface forming a suction cup adapted for securing the probe to the fetus to be monitored, and being comprised entirely of a conductive hydrogel which is adhesive under both wet and dry conditions;
- a sensor carried by said body and detecting at least one fetal parameter; and
- means for communicating the fetal parameter detected by said sensor from said sensor to a monitor.

15. A non-invasive fetal heart rate probe adapted for attachment to the presenting part of a fetus and monitoring a fetal heart rate during labor and delivery, said probe comprising:
- a body having a concave surface forming a suction cup adapted for securing the probe to the fetus to be monitored, and being comprised of a conductive hydrogel which is adhesive under both wet and dry conditions;
- a first sensor carried by said body and detecting a fetal heart rate;
- means for communicating the fetal heart rate detected by said first sensor from said first sensor to a monitor;
- a second sensor carried by said body and detecting reference signals;
- means for communicating the reference signals detected by said second sensor from said second sensor to the monitor; and
- means for electrically insulating said first sensor from said second sensor, said insulating means disposed between said first and said second sensors.

16. A non-invasive fetal heart rate probe as recited in claim 15 wherein said hydrogel of said body is prepared from at least acrylic acid and an alcoholamine.

17. A non-invasive fetal heart rate probe as recited in claim 16 wherein said alcoholamine of said hydrogel of said body is diisopropanolamine.

18. A non-invasive fetal heart rate probe as recited in claim 17 wherein said hydrogel of said body is prepared from water, acrylic acid, a photoinitiator, a crosslinking agent, diisopropanolamine and an electrolyte.

19. A non-invasive fetal heart rate probe as recited in claim 18 wherein said hydrogel of said body is prepared from about 35–40% water, 15–30% acrylic acid, 0.3–0.4% photoinitiator, 0.05–0.20% crosslinking agent and 25–30% diisopropanolamine.

20. A non-invasive fetal heart rate probe as recited in claim 19 wherein said hydrogel of said body is prepared from about 39% water, 29% acrylic acid, 0.35% 2-hydroxy-2-methyl-1-phenyl- propane-1-1one, 0.10% polyethylene glycol (400) diacrylate and 28% diisopropanolamine.

21. A non-invasive fetal heart rate probe as recited in claim 18 wherein said hydrogel of said body is prepared from about 38% water, 16% acrylic acid, 0.35% 2-hydroxy-2-methyl-1-phenyl-propane- 1-one, 0.15% polyethylene glycol (400) diacrylate and 28% diisopropanolamine and 13% vinyl pyrrolidone.

22. A non-invasive fetal heart rate probe as recited in claim 15 wherein said body is "V"-shaped.

23. A non-invasive fetal heart rate probe as recited in claim 15 wherein said body has a diameter of 10–20 mm.

24. A non-invasive fetal heart rate probe as recited in claim 15 wherein said body is comprised entirely of said conductive hydrogel.

25. A non-invasive fetal heart rate probe as recited in claim 15 wherein said body further comprises a shell, said conductive hydrogel coated on said shell and forming said concave surface of said body facing the fetus.

26. A non-invasive fetal heart rate probe as recited in claim 15 wherein said shell is polymeric.

27. A non-invasive fetal heart rate probe as recited in claim 25 wherein said shell has an outer perimeter forming a member which is one of a ledge and a ridge isolating said conductive hydrogel from fluids in the environment surrounding the probe.

28. A non-invasive fetal heart rate probe as recited in claim 27 wherein said member formed by said outer perimeter of said shell is a ridge having a top edge and a lower edge and wherein said conductive hydrogel extends to said top edge of said ridge.

29. A non-invasive fetal heart rate probe as recited in claim 27 wherein said member formed by said outer perimeter of said shell is a ledge having a side surface, a top surface, and a bottom surface and wherein said conductive hydrogel is disposed on said top surface.

30. A non-invasive fetal heart rate probe as recited in claim 15 wherein said first sensor is embedded in said conductive hydrogel.

31. A non-invasive fetal heart rate probe adapted for attachment to the presenting part of a fetus and monitoring a fetal heart rate during labor and delivery, said probe comprising:
- a body having a "V"-shaped suction cup adapted for securing the probe to the fetus to be monitored, said body having:
  - (a) a thermoplastic shell with an outer perimeter forming one of a ledge and a ridge, and
  - (b) a conductive hydrogel formed from the polymerization of a hydrogel precursor formulation comprising water, acrylic acid, a photoinitiator, a crosslinking agent, diisopropanolamine, and an electrolyte, said conductive hydrogel being adhesive under both wet and dry conditions, coated on said shell and forming a concave surface facing the fetus;

a first sensor carried by said body and detecting a fetal heart rate;

means for communicating the fetal heart rate detected by said first sensor from said first sensor to a monitor;

a second sensor carried by said body and detecting reference signals; and means for communicating the reference signals detected by said second sensor from said second sensor to the monitor, whereby one of said ledge and said ridge isolates said conductive hydrogel from fluids in the environment surrounding the probe.

32. A non-invasive fetal probe adapted for attachment to the presenting part of a fetus and monitoring at least one fetal parameter during labor and delivery, said probe comprising:

a body having:
 (a) a shell with an an outer perimeter forming a ridge having a top edge and a lower edge, and
 (b) a concave surface forming a suction cup adapted for securing the probe to the fetus to be monitored, and
 (c) a conductive hydrogel coated on said shell and forming said concave surface of said body, said conductive hydrogel being adhesive under both wet and dry conditions and extending to said top edge of said ridge and said ridge isolating said conductive hydrogel from fluids in the environment surrounding the probe;

a sensor carried by said body and detecting said at least one fetal parameter; and means for communicating the fetal parameter detected by said sensor from said sensor to a monitor.

33. A non-invasive fetal probe adapted for attachment to the presenting part of a fetus and monitoring at least one fetal parameter during labor and delivery, said probe comprising:

a body having:
 (a) a shell with an an outer perimeter forming a ledge having a side surface, a top surface, and a bottom surface, and
 (b) a concave surface forming a suction cup adapted for securing the probe to the fetus to be monitored, and
 (c) a conductive hydrogel coated on said shell and forming said concave surface of said body, said conductive hydrogel being adhesive under both wet and dry conditions and disposed on said top surface of said ledge and said ledge isolating said conductive hydrogel from fluids in the environment surrounding the probe;

a sensor carried by said body and detecting said at least one fetal parameter; and means for communicating the fetal parameter detected by said sensor from said sensor to a monitor.

* * * * *